(12) United States Patent
Zoltan et al.

(10) Patent No.: US 7,758,552 B2
(45) Date of Patent: Jul. 20, 2010

(54) TUBE CLAMP, AND TUBE CLAMP SET FOR USE WITH AN INFUSION PUMP

(75) Inventors: Hubert Zoltan, La Placette (FR); Gilbert Poncon, Pommiers la Placette (FR); Andreas Wilmers, Friedberg (DE); Jean-Marc Plazy, Meylan (FR)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 1239 days.

(21) Appl. No.: 11/287,944

(22) Filed: Nov. 28, 2005

(65) Prior Publication Data

US 2006/0079849 A1    Apr. 13, 2006

Related U.S. Application Data

(63) Continuation of application No. 10/117,317, filed on Apr. 5, 2002, now abandoned, which is a continuation of application No. PCT/DE00/03282, filed on Sep. 20, 2000.

(30) Foreign Application Priority Data

Oct. 5, 1999    (DE) ................................ 199 47 973

(51) Int. Cl.
*A61M 5/00*    (2006.01)

(52) U.S. Cl. ............... 604/250; 604/167.01; 604/170.01

(58) Field of Classification Search ................. 604/250, 604/256, 167, 34, 265, 283, 905, 167.01–167.06, 604/170.01

See application file for complete search history.

(56) References Cited

U.S. PATENT DOCUMENTS

| 3,247,852 | A |   | 4/1966 | Schneider |
| 3,766,925 | A |   | 10/1973 | Rubricius |
| 5,453,098 | A | * | 9/1995 | Botts et al. ................... 604/249 |
| 5,817,116 | A |   | 10/1998 | Takahashi et al. |
| 5,951,519 | A | * | 9/1999 | Utterberg ............... 604/167.01 |

FOREIGN PATENT DOCUMENTS

| EP |   | 0 637 456 A | 2/1995 |
| EP |   | 0 767 691 B1 | 7/1999 |
| WO |   | WO 96 00598 A | 1/1996 |
| WO |   | WO 99 18377 A | 4/1999 |

* cited by examiner

*Primary Examiner*—Kevin C Sirmons
*Assistant Examiner*—Phillip Gray
(74) *Attorney, Agent, or Firm*—Westerman, Hattori, Daniels & Adrian, LLP

(57) ABSTRACT

A tube clamp is disclosed for optional opening and closing of tubes such as infusion tubes, an infusion pump, an infusion tube set and the combination thereof, the tube clamp comprising means for opening or closing the tube clamp which interacts with a part of the infusion pump which is a lever for locking and unlocking a door in the pump, wherein an automatic opening and closing of the tube clamp can be realized without a relative movement of the tube clamp and the tube.

22 Claims, 3 Drawing Sheets

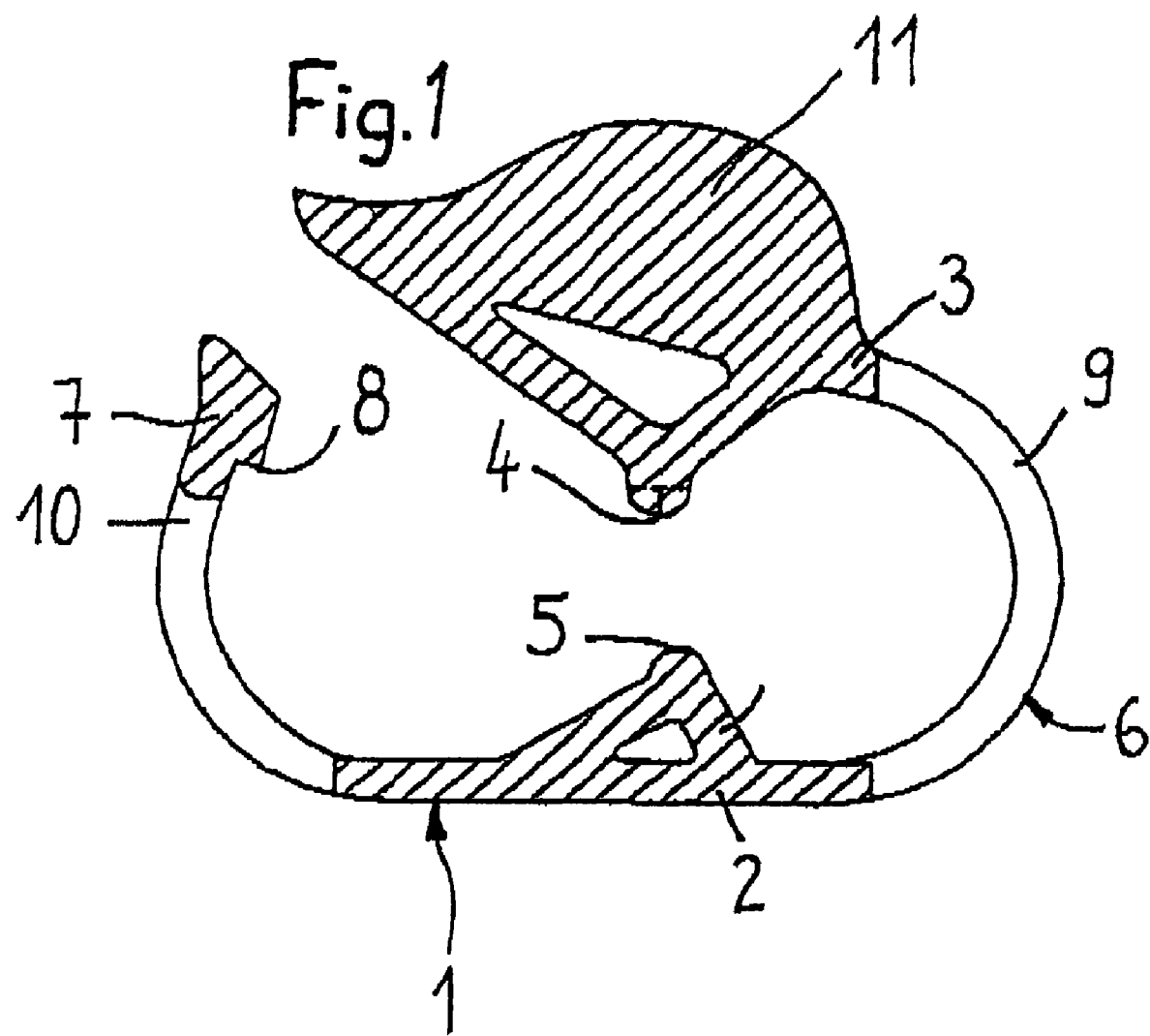

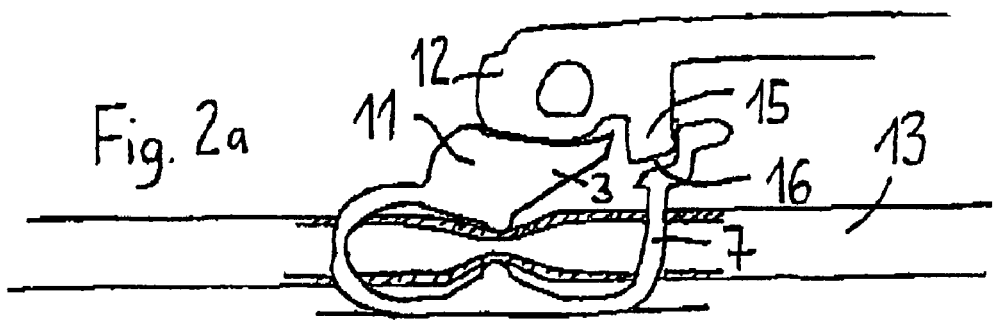
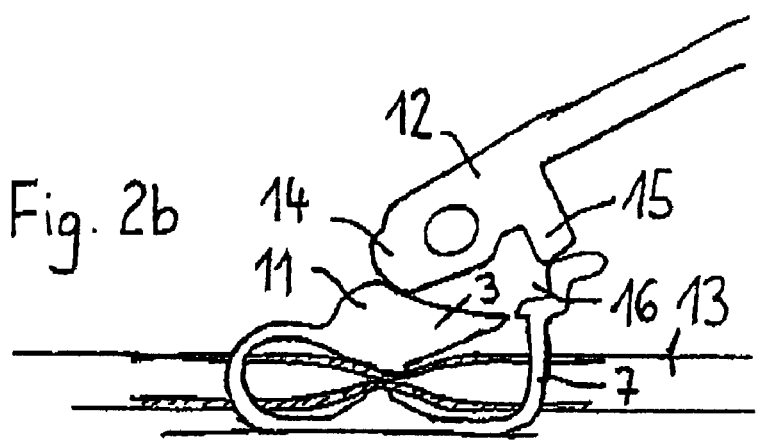
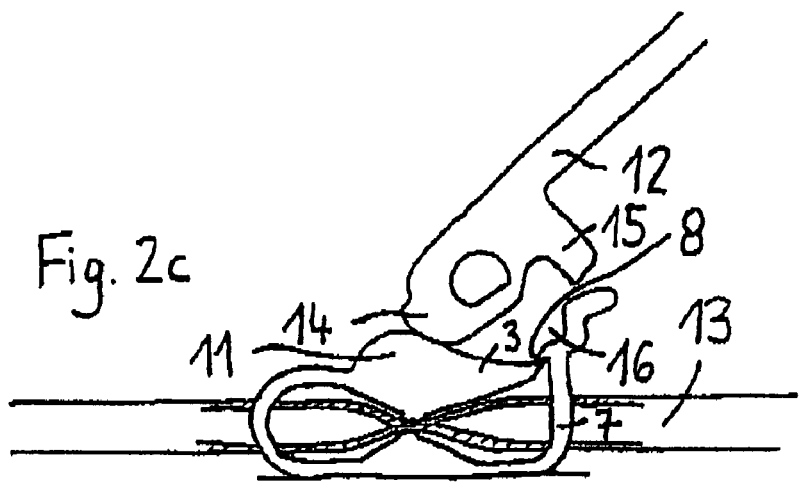
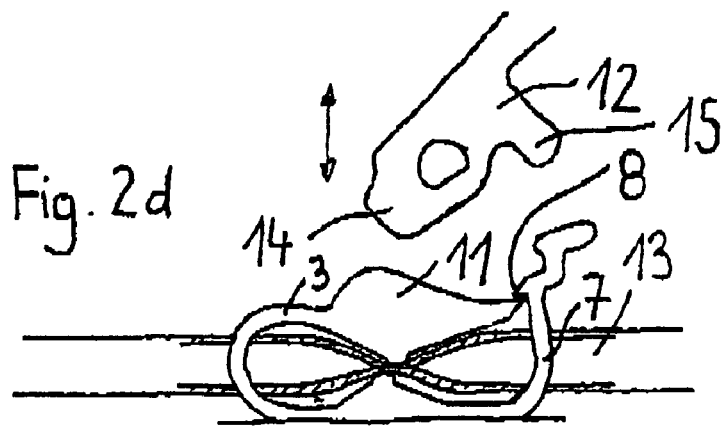

TUBE CLAMP, AND TUBE CLAMP SET FOR USE WITH AN INFUSION PUMP

CROSS-REFERENCES TO RELATED APPLICATIONS

The application is a continuation of prior filed U.S. application Ser. No. 10/117,317 filed Apr. 5, 2002 now abandoned, which is a continuation of prior filed copending PCT International application no. PCT/DE00/03282, filed Sep. 20, 2000, which designated the United States and on which priority is claimed under 35 U.S.C. §120 and which claims the priority of German Patent Application, Serial No. 199 47 973.9, filed Oct. 5, 1999, pursuant to 35 U.S.C. 119(a)-(d).

BACKGROUND OF THE INVENTION

The invention relates, in general, to a combination of an infusion pump with an infusion tube set wherein a tube is guided through a tube clamp for selectively closing and opening of tubes, for example infusion tubes, and in particular to a tube clamp essentially shaped as a shackle of U-shaped configuration with rigid legs, whose inner surface have projections configured with cooperating pinching edges and a flexible web by means of which the legs may be spread apart into a diverging position; with the first leg terminating in a flexible deflectable spring latch configured to point in a direction of the second leg and formed with an inner ledge surface for engagement of a free end of the second leg when the legs are squeezed together, and wherein the web and the spring latch are provided with openings for guiding the infusion tube therethrough.

The invention relates also to an infusion pump with a door that can be locked and unlocked for selective insertion and removal of a tube which has been placed in the tube clamp, and wherein the tube clamp can be selectively opened or locked, or respectively may be engaged in a locked position.

The invention also relates to an infusion tube set with a tube guided through the tube clamp for selectively opening and closing the tube.

A tube clamp of the type as described in the foregoing paragraphs is for example known from EP 0637 456 A1. In an open position, such tube clamps are resting loosely at the tube, thereby not obstructing the flow in the tube. When the legs of the clamp are pressed together until the spring latch engages, the clamp retains the locked position, in which the tube is being firmly pinched together. The locked position is easily unlocked with one hand, whereby the spring latch with the cam for engagement outside is bent back, thereby releasing the leg that has been locked in.

Tube clamps of this type are used also in infusion sets as afore-described.

From U.S. Pat. No. 5,817,116, a device is known for use in a medical application where removal of a tube, especially a fast removal of the device from the patient can be realized, for example during an earthquake or in a fire. By means of the device, a medical tube, which is connected to the patient, can be pinched-off at two points, so that the tube can be cut between the two pinch-off points.

In EP 0767 691 B1 an infusion set is described, showing slidable locking means, which are disposed with an opening for the tube. It is provided that, in a first position, the tube is guided through an area of the opening with sufficiently large dimension so as to allow the flow of the infusion matter through the tube, and in a second position the tube penetrates through an area of the opening with dimension substantially smaller than the tube diameter, so that the tube is thereby closed in liquid tight manner. A latch and an engaging hook are provided, which are disposed in such a manner, that the locking means are sliding from the first to the second position when opening the infusion set and upon closing it, from the second to the first position.

A drawback of this embodiment is that the tube and the locking means are moving relative to one another, which can lead to an unwanted jamming of the tube. In addition, there is the drawback that this relative movement causes wear and tear on the tube.

SUMMARY OF THE INVENTION

According to one aspect of the invention a tube clamp is provided, wherein automatic locking and opening of the tube clamp can be realized without the relative movement between the tube clamp and the tube. As a further aspect a suitable infusion pump and an infusion tube set with an integrated tube clamp is provided.

These aspects and others is realized in accordance with the invention by providing an improved combination of an infusion pump and an infusion tube set wherein a tube is guided through a tube clamp which is designed to obviate the aforestated shortcomings and drawbacks and which is configured for closing the tube when the tube clamp is engaged in a locked position; wherein the infusion pump is provided with an actuating member for cooperative engagement with a part of the tube clamp for closing or opening the tube clamp, and an infusion tube set wherein the tube is guided through the tube clamp for a selective opening and closing of the tube; and wherein the tube clamp comprises a shackle of generally U-shaped configuration, said shackle having first and second rigid legs provided with inside projections interacting with one another as pinch-off edges, and a flexible web interconnecting the legs and spreading the legs into a diverging position, said first leg terminating in a flexible spring latch which is configured to point in a direction of the second leg and formed with an undercut to define an inner ledge surface for engagement of a free end of the second leg, when the legs are squeezed together, and wherein the web and the spring latch are provided with openings for guiding the tube therethrough; the tube having actuating means responsive to a force exerted by the actuating member of the infusion pump for moving the second leg into engagement with the ledge surface of the spring latch to thereby clamp the tube in conjunction with the pinch-off edges.

In accordance with the invention the tube clamp is provided with means for closing the tube clamp and means for opening the tube clamp in such a manner, that by means of a force exerted by an actuating member upon the tube clamp opening or locking of the tube clamp is realized.

In accordance with another aspect of the invention, it is provided that the means for closing the tube clamp is configured as an element disposed at the tube clamp, on which a part of the pump can impart a vertical force upon the second leg of the tube clamp.

In accordance with one embodiment of the invention it is provided, that the means for closing the tube clamp is configured with an arched portion at the outer surface of the second leg, from which at least one part of a lever of the infusion pump is able to perform a roll-off motion.

It is an aspect of the present invention that the lever which is already present for locking and unlocking the door can also be used for opening and closing the tube. Through suitable adaptation of the tube clamp, a cooperative interaction of the tube clamp with the lever can be realized.

When opening the door, the lever carries out a rocking motion so that during this motion the end of the lever can roll off the arched portion at the outside of the second leg of the tube clamp and thereby brought into locked position. When locking the door, the process is reversed.

Advantageously, the arched portion has a toothed surface for interacting with a complementary tooth surface of the rocking lever to thereby prevent a slipping between the means which are disposed at the leg of the tube clamp for engagement with the lever and the lever itself.

It is within the scope of the invention, that the tube, which is placed in the tube clamp, is clamped liquid proof by means of the cooperative engagement with the closing means and the lever.

In another aspect of the invention, the tube clamp is latched through the co-operative engagement of the closing means of the tube clamp with the lever.

It is also within the scope of the invention, that the means for opening the tube clamp at the spring latch are configured as an element for cooperative engagement with at least one part of the rocking lever of the infusion pump, whereby the spring latch is being pushed away from the second leg.

Also within the scope of the invention, is an infusion pump with an infusion tube set, wherein the infusion pump is provided with a door activated for closing and opening by a lever, for inserting or removing a tube, which tube is guided through a tube clamp for selectively opening or closing the tube, respectively for the tube clamp being in a locked position, and wherein the infusion pump is provided with an actuating member by which a force is exerted upon the tube clamp whereby locking of the tube clamp is realized.

Within the scope of the invention is also the use of an infusion tube set, wherein a tube is guided through a tube clamp, by means of which the tube may be selectively opened or closed, respectively the tube clamp can be engaged in a locked position in an infusion pump.

One of the advantages of the invention is that it utilized the rocking lever already available, opening and closing of the tube can be realized in coordination with the locking respectively, the unlocking of the door without the need for a relative movement between the tube clamp and the tube.

BRIEF DESCRIPTION OF THE DRAWING

Other features and advantages of the present invention will be more readily apparent upon reading the following description of currently preferred exemplified embodiments of the invention with reference to the accompanying drawing, in which:

In the following paragraphs, the invention is described in connection with exemplary embodiments. It is shown in:

FIG. 1 a tube clamp according to the invention;

FIG. 2a-2d the locking of the tube clamp according to the invention by means of a lever;

DETAILED DESCRIPTION OF PREFERRED EMBODIMENTS

Figure 3A:
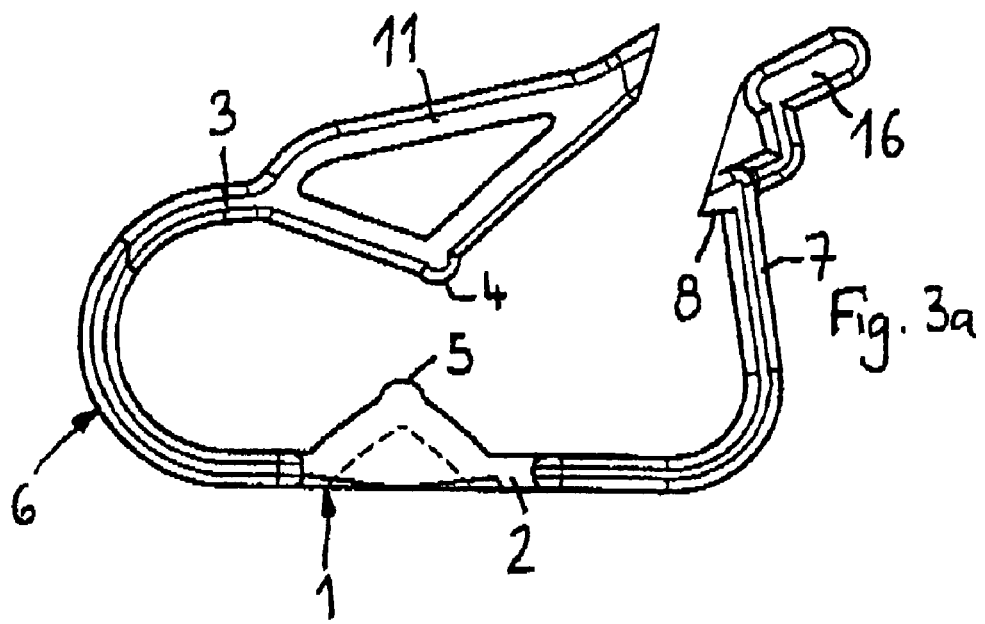
FIG. 3a-3c further embodiments of a tube clamp according to the invention shown in a side view, in a sectional view and a top plan view.

Throughout all the Figures, same or corresponding elements are generally indicated by same reference numerals.

Turning now to the drawing, and in particular to FIG. 1, there is shown a tube clamp 1 that has a first leg 2 and a second leg 3 with their respective inner surfaces configured as projections 4, 5 which are acting as cooperating pinching edges and which are connected by means of a bending-elastic web 6 by which the legs 2, 3 can be brought in diverging position and spread apart.

A bending-elastic spring latch 7, which serves to keep the tube clamp 1 in the locked position, is connected to the free end of the first leg and is curved in the direction of the second leg and disposed with an inward pointing lug 8, which the free end of the second leg engages in a locking position when the legs 2, 3 are pressed together. The web 6 and the spring latch 7 are provided with openings 9, 10 for guiding the tube therethrough. The second leg is provided at its outer surface with means 11 for locking the tube clamp which is configured as an arched portion that corresponds in the present example with the shape of the lever and upon which the end 14 of the lever 12 can roll off.

FIGS. 2a-2d illustrate the cooperation of lever 12 and the means 11 for locking the tube clamp and the means 16 for opening the clamp. In its starting position (according to FIG. 2a) the shoulder 15 of lever 12 is resting on the element 16 of tube clamp 1 configured with a step for resting the shoulder 15, and wherein element 16 is disposed approximately perpendicular to spring latch 7, and the tube 13 extends through tube clamp 1 without any particular pressure exerted by the projections 4, 5 onto the tube 13. The liquid can circulate within tube 13.

Starting from the positions shown in FIG. 2a, the lever 12 starts its rotational motion and exerts pressure upon the means 11 through end 14, for co-operating with lever 12, as shown the arched portion 11. The projections 4, 5 are beginning to pinch the tube 13.

As seen in FIG. 2b, tube 13 has been pressed together firmly by means of the end 14 of lever 12, so that the tube is pinched liquid tight. Due to the roll off motion of the end 14 of lever 12 upon camber 11, the second leg 3 of the tube clamp 1 is being moved towards the spring latch 7 and pressed downwardly. Simultaneously, the web 6 is resiliently restored into its starting position because the shoulder 15 of lever 12 no longer presses upon element 16.

FIG. 2c shows the moment where the second leg 3 engages in the projection 8 of spring latch 7, after the lever 12 has been further rotated.

As is shown in FIG. 2d, after locking the tube clamp 1, the lever 12 can be lifted.

Due to considerations of storage, as a rule, the tube set will be distributed with the tube clamp in open position. Prior to application, the user will close the tube clamp and inserts the tube set into the pump. The pump must now be ready to open the tube clamp. Opening of tube clamp 1 takes place in reverse order to the one shown in FIGS. 2a-2d. When opening, a force is applied approximately parallel to spring latch 7 upon the step of element 16 whereby a torque is created which leads to the expansion of the tube clamp.

It should be noted, that instead of step 16 any other element can be provided at tube clamp 1 for cooperation with lever 12, so long as by this cooperation the spring latch 7 can be pushed away by the second leg of the tube clamp. Likewise when closing the tube clamp, it is important that the pressure is being exerted in vertical direction upon the second leg 3 of the tube clamp.

Figure 3B:
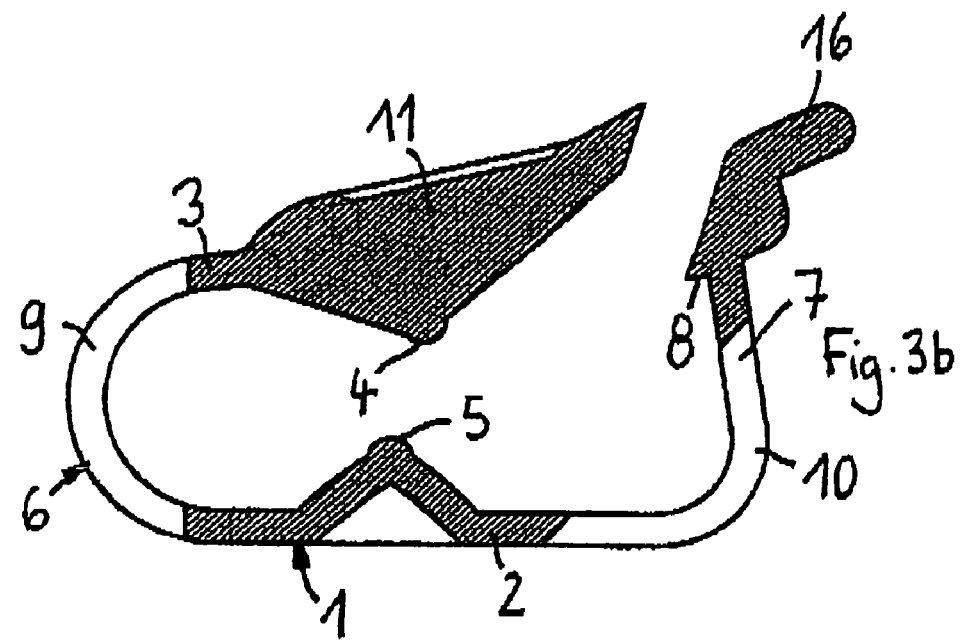
Figure 3C:
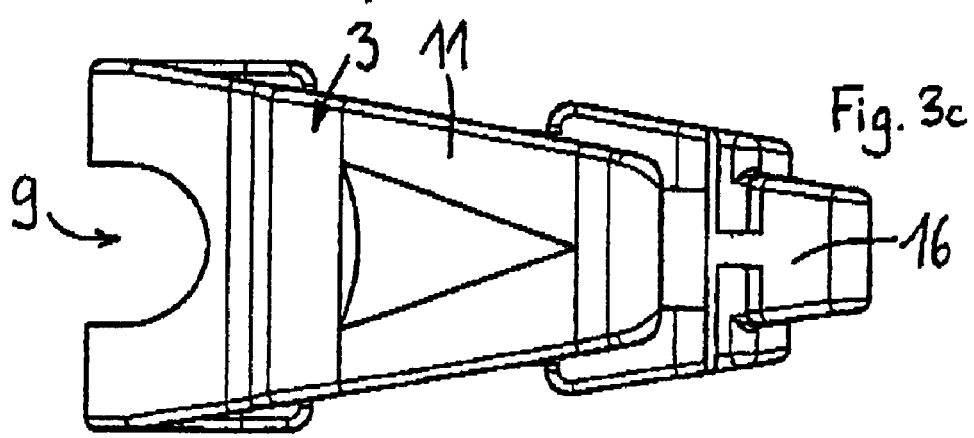

As is illustrated from FIGS. 3a to 3c, the tube clamp according to the invention can be so configured, that in lieu of the element 16 configured as a stepped shoulder, an inclined surface is provided upon which the end of the second leg moves along before engaging under the cam 8 of spring latch 7. In this embodiment the counter part 15 on the infusion pump side is in contact only with the upper portion of the stepped shoulder of element 16. By means of effecting a force approximately parallel to the spring latch 7 upon the upper portion of element 16, a torque is created which leads to the expansion of the tube clamp.

It may be desirable that a small slip is created during the roll off motion of the lever 12 from the means 11, respectively 16 when closing, respectively opening the tube clamp. This can be realized for example by the cooperating surfaces of the lever and the means 11 respectively 16 by providing a friction-increasing layer, or by arranging for corresponding teeth between them.

With a tube clamp that is automatically operated through the infusion pump it is advantageous to provide means for detection of a tube clamp in the pump, for example by an optical scanning system or an electrical scanning system (e.g. by using an electrical conducting plastic for the tube clamp.

While the invention has been illustrated and described as embodied in a tube clamp and infusion pump set, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and their equivalents.

What is claimed is:

1. A tube clamp, for selectively closing and opening tubes, being configured as an essentially U-shaped shackle having rigid legs provided with inside projections that interact with each other as pinch-off edges, a flexible web by means of which the legs can be spread into a diverging position and a flexible spring latch connected to the free end of the first leg and curving towards the second leg, said latch having an inward-pointing cam behind which the free end of the second leg engages in the locking position when the legs are pressed together, the web and the spring latch being provided with openings for guiding the tube therethrough, wherein the tube clamp has means for closing the tube clamp in response to pressure exerted by an actuating member of an infusion pump, wherein the means for closing the tube clamp comprises an arched surface located on an face of the second leg facing away from the first leg, said arched surface protruding in a direction away from the first leg, wherein the arched surface extends along a longitudinal direction of the second leg on both sides of a line coinciding with a main protruding direction of the inside projection of the second leg.

2. A tube clamp closing system, comprising:
the tube clamp of claim 1, and
an actuating member for closing the tube clamp,
wherein the actuating member comprises an arched surface configured so as to face the arched surface of the tube clamp and to push the second leg down by applying a pressure on the second leg in a direction transverse to a main direction of the first leg when the actuating member is moved rotationally in order to close the tube clamp.

3. The system of claim 2, wherein the actuating member is a rocking lever, wherein the rocking lever moves rotationally without slippage between the arched surface of the rocking lever and the arched surface of the tube clamp.

4. The system of claim 3, wherein the arched surface of the tube clamp has a toothed surface for interacting with a complementary toothed surface of the arched surface of the rocking lever.

5. The system according to claim 2, wherein a tube inserted into the tube clamp is clamped shut in liquid-tight manner between the inside projections of the tube clamp by interaction of the arched surface of the tube clamp with the arched surface of the actuating member.

6. A combination of an infusion pump and an infusion tube set, the tube being guided through a tube clamp with which the tube can be selectively opened and/or closed, wherein said combination comprises:
the system of claim 2,
an infusion pump having a lockable and unlockable door for insertion and removal of a tube guided through the tube clamp that can be selectively opened and/or closed and is engageable in the locking position, wherein the actuating member, in operation, also locks and unlocks the door,
and an infusion tube set, the tube being guided through the tube clamp with which the tube can be selectively opened and/or closed.

7. An infusion tube set comprising a tube guided through the tube clamp of the system of claim 2, with which clamp the tube can be selectively closed.

8. An infusion pump having a lockable and unlockable door for insertion and removal of a tube guided through a tube clamp that can be selectively opened and/or closed and is engageable in the locking position, wherein the infusion pump is provided with the system of claim 2, wherein said actuating member, in operation, also locks and unlocks the door.

9. The infusion pump of claim 8, wherein the actuating element is a rocking lever that, in operation, carries out a rocking motion so that the end of the lever rolls off the arched portion of the tube clamp to bring the tube clamp into closed position, and that carries out a reverse rocking motion so that the lever pushes the spring latch away from the second leg to bring the tube clamp into open position.

10. The infusion pump of claim 9, wherein the rocking lever carries out the rocking motion when opening the door and the reverse rocking motion when closing the door.

11. The combination of claim 6, wherein the actuating element is a rocking lever that, in operation, carries out a rocking motion so that the end of the lever rolls off the arched portion of the tube clamp to bring the tube clamp into closed position, and that carries out a reverse rocking motion so that the lever pushes the spring latch away from the second leg to bring the tube clamp into open position.

12. The combination of claim 11, wherein the rocking lever carries out the rocking motion when opening the door and the reverse rocking motion when closing the door.

13. The system of claim 2, wherein the actuating element is a rocking lever that carries out a rocking motion so that the end of the lever rolls off the arched portion of the tube clamp to bring the tube clamp into closed position, and that carries out a reverse rocking motion so that the lever pushes the spring latch away from the second leg to bring the tube clamp into open position.

14. The tube clamp of claim 1, wherein the arched surface of the tube clamp has a toothed surface for interacting with a complementary toothed surface of a rocking lever.

15. An infusion tube set comprising a tube guided through the tube clamp of the clamp of claim 1, with which clamp the tube can be selectively closed.

16. The tube clamp of claim 1, wherein the arched surface of the tube clamp has a friction-increasing layer.

17. The system of claim 2, wherein the arched surface of the tube clamp has a friction-increasing layer.

18. The system of claim 2, wherein the actuating member comprises a shoulder configured so as to cooperate with the flexible spring latch to push the spring latch away from the second leg in order to open the tube clamp.

19. The system of claim 18, wherein the flexible spring latch comprises a step which cooperates with the shoulder of the actuating member in order to push the spring latch away from the second leg.

20. The system of claim 18, wherein the flexible spring latch comprises a cam which cooperates with the shoulder of the actuating member, so that a movement of the actuating member in a direction approximately parallel to the spring latch creates a torque that pushes the spring latch away from the second leg.

21. The tube clamp of claim 1, wherein the flexible spring latch comprises a step for cooperating with a shoulder of an actuating member so as to push the spring latch away from the second leg.

22. The tube clamp of claim 1, wherein the flexible spring latch comprises a cam for cooperating with a shoulder of an actuating member, so that a movement of the actuating member in a direction approximately parallel to the spring latch creates a torque that pushes the spring latch away from the second leg.

* * * * *